United States Patent [19]

Ehnholm

[11] Patent Number: 5,289,125
[45] Date of Patent: Feb. 22, 1994

[54] METHOD OF ELECTRON SPIN RESONANCE ENHANCED MRI

[75] Inventor: Gosta J. Ehnholm, Helsinki, Finland

[73] Assignee: Instrumentarium Corporation, Helsinki, Finland

[21] Appl. No.: 790,209

[22] Filed: Nov. 8, 1991

[30] Foreign Application Priority Data

Nov. 12, 1990 [GB] United Kingdom ............... 9024527

[51] Int. Cl.⁵ .............................................. G01R 33/20
[52] U.S. Cl. ..................................... 324/309; 324/316
[58] Field of Search ............... 324/316, 309, 307, 318, 324/300

[56] References Cited

U.S. PATENT DOCUMENTS

| | | | |
|---|---|---|---|
| 4,620,154 | 10/1986 | Inouye | 324/309 |
| 4,719,425 | 1/1988 | Ettinger | |
| 5,144,238 | 9/1992 | Ehnholm | 324/316 |
| 5,154,603 | 10/1992 | Sepponen | 324/316 |

FOREIGN PATENT DOCUMENTS

| | | |
|---|---|---|
| 0302742 | 8/1989 | European Pat. Off. |
| 9002343 | 3/1990 | PCT Int'l Appl. |
| 8810419 | 12/1990 | PCT Int'l Appl. |
| 2164155 | 12/1986 | United Kingdom |

*Primary Examiner*—Michael J. Tokar
*Assistant Examiner*—Raymond Y. Mah
*Attorney, Agent, or Firm*—Chilton, Alix & Van Kirk

[57] ABSTRACT

A method of electron spin resonance enhanced magnetic resonance imaging of a paramagnetic substance-containing sample wherein an image of at least part of the sample is generated from a data set produced by manipulation of enhanced free induction decay signals detected under at least two different sets of operational parameters. The operating parameters which are varied to produce the different sets include the timing of the exposure of the sample to magnetic field gradients and spin resonance stimulating radiations and, optionally, also the amplitude and frequency distribution of the electron spin resonance stimulating radiations. The manipulation of the detected signals produces, for individual image elements, a normalized signal representative of the difference between signals for that element under the different sets of operational parameters.

5 Claims, 1 Drawing Sheet

METHOD OF ELECTRON SPIN RESONANCE ENHANCED MRI

BACKGROUND OF THE INVENTION

1. Field of the Invention

This invention relates to improvements in and relating to magnetic resonance imaging (MRI) and in particular to improvements in electron spin resonance enhanced magnetic resonance imaging.

2. Description of the Related Art

Magnetic resonance imaging is a diagnostic imaging technique that is gaining widespread acceptance among physicians. It is particularly attractive as it does not involve exposing the patient to radioactivity or ionizing radiation.

An improved modification of MRI, which utilizes the phenomenon of dynamic nuclear polarization, otherwise known as the Overhauser effect, to achieve significant enhancement of the magnetic resonance (MR) signals from which the MR images are generated, has recently been suggested. In this technique, variously termed Electron Spin Resonance Enhanced Magnetic Resonance Imaging (ESREMRI), Overhauser Magnetic Resonance Imaging (OMRI) and Proton Electron Double Resonance Imaging (PEDRI), the subject is irradiated with radiation of a frequency selected to stimulate electron spin resonance transitions in a paramagnetic substance, e.g. a stable free radical, distributed within the subject. Interaction between the stimulated electron spin system and the nuclear spin system (generally water protons) responsible for emitting the free induction delay (FID) signals from which the MR image is generated results in a relative overpopulation of the excited state of the nuclear spin system and as a result an enhancement of the FID signals. ESREMRI is discussed for example in WO-A-88/10419 (Leunbach) and related techniques are discussed in U.S. Pat. No. 4,719,425 (Ettinger), WO-A-90/02343 (Leunbach) and EP-A-302742 (Lurie).

Where MRI and ESREMRI have been used for diagnostic imaging, this has generally been to provide structural, i.e. anatomical, information. These imaging techniques can however be used to image other physical, chemical or biological parameters, for example temperature, contrast agent presence or distribution, blood flow, etc., insofar as these parameters exert a measurable effect on the magnetic resonance (FID) signals. The present invention is concerned particularly with this so-called parameter imaging. One problem generally faced in parameter imaging is that the FID signal is affected by many factors besides the parameter of interest and that if these factors vary within the sample or subject under study then variations in image intensity cannot be simply correlated to the variations in the parameter of interest. At present therefore MR images are utilized mostly for the anatomical information they provide with the image intensity being used to delineate anatomical structures rather than being considered to have any quantitative significance.

In conventional MRI, FID signal intensities are dependant on the spin-lattice and spin-spin relaxation times ($T_{1p}$ and $T_{2p}$ respectively) of the imaging nuclei, on the density of the imaging nuclei (generally the proton density) and occasionally on a flow velocity. Although it is possible to some extent to distinguish between these parameters by the use of appropriate imaging sequences, one is still faced by the problem of interpreting the significance of the relaxation times which have no clear diagnostic significance unlike primary parameters such as temperature, pH, oxygen tension, viscosity, etc.

SUMMARY OF THE INVENTION

The present invention is based on the realization that the factors affecting the intensity of enhanced FID signals in ESREMRI are such, that by comparison and manipulation of enhanced FID signals obtained under different operating parameters, greater diagnostic significance can be ascribed to variations in intensity in the resultant images, i.e., images may be generated from which an indication of the distribution of physical, chemical or biological parameters, rather than simply structural/anatomical information, may be obtained.

Thus viewed from one aspect the invention provides a method of electron spin resonance enhanced magnetic resonance imaging of a paramagnetic substance-containing sample wherein an image of at least part of a said sample is generated from a data set produced by manipulation of enhanced free induction decay signals detected under at least two different sets of operational parameters, said parameters including the timing of the exposure of said sample to magnetic field gradients and spin resonance stimulating radiations and optionally also the amplitude and frequency distribution of the electron spin resonance stimulating radiations and said manipulation producing for individual image elements a normalized signal representative of the difference between signals for that element under said different operational parameters.

BRIEF DESCRIPTION OF THE DRAWING

The present invention may be better understood and its numerous objects and advantages will become apparent to those skilled in the art by reference to the accompanying drawing wherein.

DESCRIPTION OF THE PREFERRED EMBODIMENTS

Figure 1:
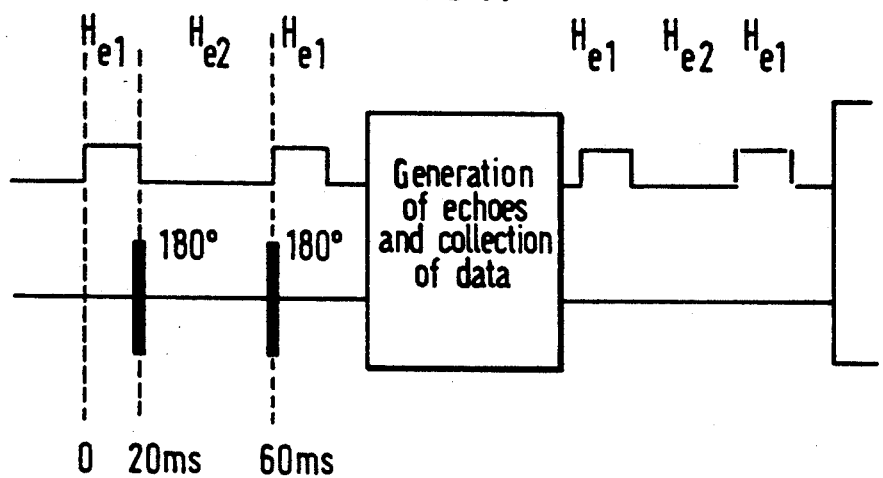
FIG. 1 represents the timing sequence within an imaging method according to the invention, FIG. 1 illustrating the technique of proton polarization averaging.

The method of the present invention is particularly characterised by the generation of the image from "normalized difference signals", i.e. the signal for an image element is a ratio of one value representative of a difference between signals generated under different operational conditions and a second value representative of an average of signals generated under different operational conditions, e.g. a signal $\Delta A/\overline{A}$ where $\overline{A}$ is a mean signal amplitude for an image element (voxel or pixel) and $\Delta A$ is the difference between signal amplitudes for that element for signals corresponding to two different sets of operational parameters. As is described below for the example of the saturation recovery MRI pulse sequence, by generating $\Delta A/\overline{A}$ one substantially eliminates the effect on image intensity of factors such as $T_{1p}$ and $T_{2p}$ leaving the resultant image more strongly responsive to other factors which have clearer diagnostic significance.

The method of the invention is differentiated from the ESREMRI (PEDRI) techniques of Lurie and Ettinger (supra) in which the ESREMRI image is generated by manipulation of two data sets, a first corresponding to an enhanced FID signal obtained with irradiation of a sample with electron spin resonance stimulating radiation (hereinafter the VHF radiation) and the second obtained without VHF irradiation (or with irradiation at a different VHF power level or a different frequency). The difference between the two data sets, before or after Fourier transformation is used to provide an image. Ettinger describes this technique as involving modulating the intensity of the VHF radiation thereby modulating the intensity of the FID signals, and extracting the modulation from the FID signal to generate an image representative of the concentration of paramagnetic species in the sample being imaged. Thus in effect Lurie and Ettinger suggest generation of ESREMRI images from an enhanced signal from which is subtracted a background signal generated under otherwise the same operational parameters. Neither Ettinger nor Lurie suggest that the intensity in the final image is quantitatively significant other than as an indication of the local concentration of the paramagnetic substance.

The method of the present invention is also different from the thermographic imaging method of Leunbach described in WO-A-90/02343 which requires the use of a paramagnetic substance having an esr transition whose frequency is temperature dependant. Thus, for example, one embodiment of Leunbach method involves irradiation at two different VHF frequencies one selected to excite a temperature invariant esr transition and the other to excite, at least in part, a temperature-variant transition, the thermographic image being generated by setting the intensity of each image element as the ratio of the intensities for that element for irradiation by the two different VHF frequencies.

Turning to the example of the saturation recovery MRI pulse sequence, this sequence involves exposing the nuclear spin population to a 90° pulse of the nuclear magnetic resonance stimulating radiation (hereinafter the RF radiation), and exposing the sample to a read out pulse after time $T_R$ to generate an echo FID signal after a further time $T_E$. It is not important for present considerations whether a gradient echo or a 180° RF pulse echo is used.

The amplitude A of the FID signal is given by $$A = M (1 - \exp(-T_R/T_{1p})) \exp(-T_E/T_{2p}) \quad (1)$$

where M is the magnitude of the equilibrium magnetization of the imaging nuclei. If $T_E$ is made much smaller than $T_{2p}$ and $T_R$ much smaller than $T_{1p}$ equation (1) can be approximated by $$A = M T_R / T_{1p} \quad (2)$$

In the case of an enhanced FID signal in ESREMRI, the magnetization value M is altered and may be expressed approximately by $$M = 330 M_o f T_{1p} R C \quad (3)$$

which combined with equation (2) gives $$A = 330 M_o f T_R R C \quad (4)$$

where R and C are respectively the $T_{1p}$ relaxivity and the concentration of the paramagnetic substance, $M_o$ is the equilibrium value of M in the absence of esr enhancement, i.e. in the absence of VHF irradiation, and f is a shape function dependant on $T_{1e}$, $T_{2e}$, $H_e$ and $\Delta H$, $T_{1e}$ and $T_{2e}$ being the spin-lattice and spin-spin relaxation times for the electrons in the paramagnetic substance, $H_e$ being the amplitude of the VHF radiation experienced by the sample and $\Delta H$ being the shift from electron spin resonance of the VHF radiation. Far from resonance f is equal to zero and at resonance it approaches 1.

Thus unlike the FID signal intensity in conventional MRI which is strongly dependant on $T_{1p}$ and $T_{2p}$, the enhanced FID signal intensity in ESREMRI is effectively independent of $T_{1p}$ and $T_{2p}$, and the unknown dependence of $T_{1p}$ and $T_{2p}$ on physical and biological parameters is no longer an obstacle to the interpretation of signal intensity.

Thus in an imaging operation where the different operational parameters still involves stimulation of the same esr transition of the same paramagnetic substance the magnitude of a normalized difference signal $\Delta A/\overline{A}$ is thus essentially independent of all factors relating to the nuclear spin system and instead is dependant on parameters that may be varied by the operator of the ESREMRI apparatus.

The exact form of the shape function f is to some extent empirical. In liquids the esr line-shape is quite close to Lorentzian and the general expression for f then becomes $$f = 1 - (1 + \gamma^2 T_{2e}^2 \Delta H^2)/(1 + \gamma^2 T_{1e} T_{2e} H_e^2 + \gamma^2 T_{2e} \Delta H^2) \quad (5)$$

where $\gamma$ is the gyromagnetic moment of the electron and with the Bloch equation at the rightmost side. This can be simplified to:

$$f = \gamma^2 H_e^2 T_{1e} T_{2e}/(\gamma^2 H_e^2 T_{1e} T_{2e} + 1 + \gamma^2 H_e^2 T_{2e} \Delta H( \quad (6)$$

Frequently there are practical constraints, especially in imaging of living subjects, on the maximum permissible VHF intensity and in such cases equation (6) may be simplified further to $$f = \gamma^2 H_e^2 T_{1e} T_{2e}/(1 + T_{2e}^2 \Delta H^2) \quad (7)$$

From equation (7) it can be seen how f is affected by two parameters that can be varied by the operator of the ESREMRI apparatus, namely $H_e$ (the VHF amplitude) and $\Delta H$ (which is proportional to the offset from resonance of the VHF frequency $F_e$). By measuring the change in f caused by a change in amplitude and in frequency, respectively, of the VHF signal both $T_{1e}$ and $T_{2e}$ can be determined. In addition, by offsetting $F_e$ in both directions around resonance one can measure a possible shift of the esr resonance frequency.

In parameter imaging, one is normally trying to ascribe a value to some primary parameter such as temperature, pH, oxygen tension, or viscosity. This can be done if that parameter influences the esr parameters $T_{1e}$, $T_{2e}$ and resonance frequency, which is often the case. For instance, the chemical surroundings of the paramagnetic centre often shift its resonance frequency, or the local oxygen concentration broadens its line width. Thus if the method of the invention is to be performed so as to generate images in which image. intensity is strongly responsive to these primary parameters one might choose the VHF amplitude $H_e$ or VHF frequency $F_e$ for example as the operational parameters which are varied. In the latter case intensity variations will have a different significance depending on whether the selected frequencies are symmetrically disposed about the resonance frequency or not, e.g. where one frequency is at resonance and one is offset. In the first case the image intensity is sensitive to the position of the esr resonance peak, in the second to its width, i.e. to $T_{2e}$. One could also change both the VHF amplitude and its frequency in order to obtain a shift in f which is as sensitive as possible for the primary parameter of interest and at the same time as insensitive as possible to other parameters.

Where, as is generally the case, the paramagnetic substance has more than one esr transition in its esr spectrum, one can select as the variation between the different operational parameter sets a variation in $F_e$ and optionally $H_e$ such that the difference signal represents a difference between signal intensities from stimulation of different esr transitions.

The difference signal (e.g. $\Delta A$) may be derived as the difference between two measurements. Sometimes it might be expedient, however, to make several measurements and define $\Delta A$ as a linear outcome of said measurements. For instance, an esr spectrum with two lines might have the distance between lines depend on temperature but the line widths on viscosity. By measuring signal intensity at four frequencies, pairwise around the centre of each line, one can compute $\Delta A$ as the difference between the average of each pair of measurements and thus substantially remove the influence of the factors influencing line widths.

One may also utilise more than one paramagnetic species in the imaging method of the invention. Thus for example one may use a combination of a first paramagnetic substance which is chemically stable and a second one which has two (or more) forms in equilibrium, with the equilibrium concentration dependent on some primary parameter, such as pH. The balance in the equilibrium will therefore determine the availability of the paramagnetic substance for an esr transition of which one value of $F_e$ is selected.

Thus viewed from a yet further aspect the invention also provides a method of imaging the distribution of two or more paramagnetic substances within a sample wherein a first said substance has a first esr transition the frequency and linewidth of which is substantially invariant in the volumes of said sample in which said first substance is distributed and a second said substance has a second esr transition the frequency or linewidth of which is variable according to the location of said second substance in said sample, said method involving exposing said sample to radiation of frequencies selected to excite said first and second esr transitions, detecting enhanced magnetic resonance signals from said sample and generating an image of said sample indicative of the distribution of said paramagnetic substance from said detected magnetic resonance signals, preferably generating said image from a data set where the signal corresponding to each image element is a value dependent on the signal for said element under the irradiation of said sample with said second radiation manipulated by, e.g. normalized by and/or with subtraction of a value dependent on the signal from said sample or for said element under irradiation with said first radiation.

$\Delta A$ would then represent a more complex quantity than $\Delta f$ which would involve $R_1C_1f_1 - R_2C_2f_2$ where $R_1$ is the relaxivity, $C_1$ the concentration and $f_1$ the shape function for the first paramagnetic substance and $R_2$, $C_2$, $f_2$ the corresponding quantities for the second paramagnetic substance. Changes in the relaxivity or the active concentration of the second substance, or indeed either substance, could be measured and thus information gained of variations in primary parameters.

One simple method of performing the method of the invention however involves generating two saturation-recovery images with $T_R$ and $T_E$ short compared to $T_{1p}$ and $T_{2p}$, respectively and with the VHF signal used for the two images having different amplitudes and/or frequencies. By taking the difference between picture signals pixel by pixel we get $$\Delta A = 330 M . \Delta f \, T_R R C$$

which is proportional to $\Delta f$. Taking the average of the two images, summing then pixel by pixel and dividing by two, the difference image is divided by the average pixel by pixel:

$$\frac{\Delta A}{A} \alpha \frac{\Delta f}{f} \qquad (9)$$

Here the denominators are formed by the averaging. The quantity $\Delta f/f$ is as such well suited for use as a secondary parameter because its dependence on the intermediary parameters $T_{1e}$, $T_{2e}$ and $\Delta H$ is more straightforward than for $\Delta f$.

For the case of a mixture of two paramagnetic substances the difference signal is $$\Delta A = 330 \, M_o T_R (f_1 R_1 C_1 - f_2 R_2 C_2)$$

Where the subscript 1 denotes signals in the first image and 2 in the second one. For simplicity one may assume that the first image contains signals produced by the effort of the first paramagnetic substance 1 and the second by the effort of the second paramagnetic substance; this is not essential and images that "mix" signals from the two substances might also be useful.

The method for forming $\Delta A/\overline{A}$ discussed above may involve subtracting two images formed at different moments of time. In these circumstances the method is sensitive to even minute changes in e.g. local concentration of agent which are difficult to control in a living body. A preferred embodiment of the method therefore involves intermingling the two images at the time of data collection.

Thus for example if the image generation involves 2-dimensional Fourier transformation with phase coding in one direction and frequency coding in the other one, which is the most common method, image data is collected line by line by forming spin echoes, each echo with different phase. To minimise the time between signals to subtract, one can make each echo twice, once for each value of $H_e$ or $F_e$. The subtraction is then done on an echo-by-echo basis rather than pixel-by-pixel. This is possible because the Fourier transform, used for constructing an image from the data is linear. Echo subtraction forms a robust method for constructing $\Delta A$; to form $\Delta A/\overline{A}$ however one must still divide the $\Delta A$ image on a pixel-by-pixel basis with the A image because division is a non-linear operation and therefore cannot be made before the Fourier transform.

Nonetheless, even without normalization the difference images, generally represented here by ΔA, may be of diagnostic value and the invention also includes within its scope methods wherein the final image generated is a difference image where the varied operational parameters include the timings of the exposure of the sample to magnetic field gradients and spin resonance stimulating radiations.

The echo subtraction method described earlier is superior to pixel subtraction. However a third method, called proton polarization averaging, is particularly useful. This technique may be illustrated by reference to FIG. 1 of the accompanying drawing which shows, in schematic form the timing sequence within an imaging method according to the invention. The box in FIG. 1 labelled "Generation of echoes and collection of data" is described further by way of exemplification with reference to FIG. 2 of the accompanying drawings which again shows a timing sequence in schematic form. Referring to FIG. 1, at time zero the sequence starts with a polarization period, for example 20 ms. The proton spins are polarized by dynamic nuclear polarization using a VHF radiation of the amplitude $H_{e1}$. At 20 ms the proton spins are inverted and a new polarizing period of length 40 ms starts. The VHF amplitude is now $H_{e2}$.

One could alternatively use a different VHF frequency during this period, instead of or in combination with the new amplitude.

Figure 2:
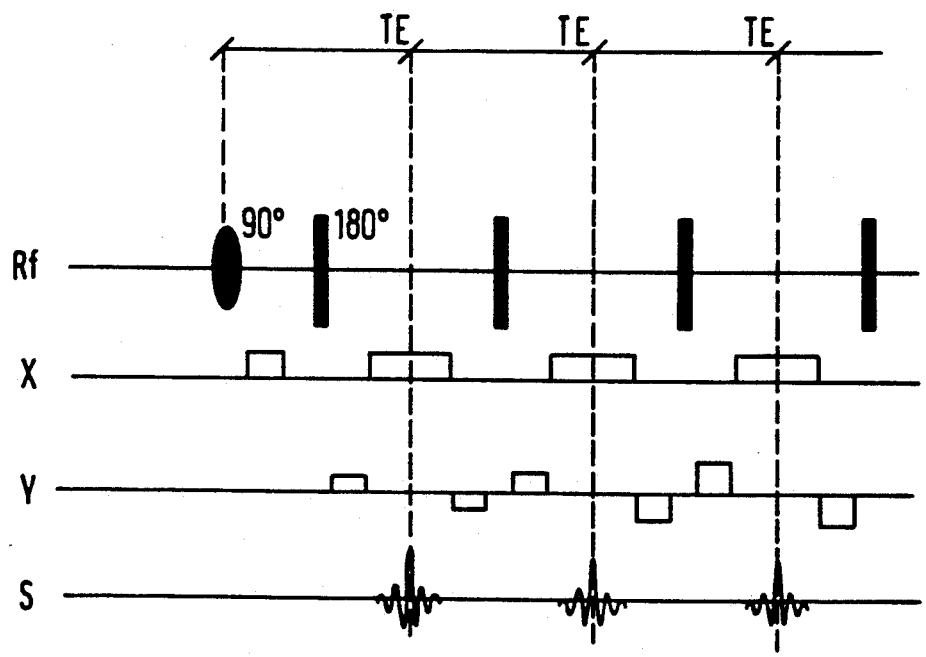
FIG. 2 is a schematic illustration of that portion of the technique illustrated in FIG. 1 which has been shown in block form in FIG. 1.

At time 60 ms the protons are again inverted and the VHF amplitude (and frequency) is returned to its previous value. At time 80 ms the polarizing VHF-signal is switched off. Soon after this the information for forming an image is extracted from the generated proton polarization. A preferred method for achieving this is illustrated by FIG. 2. The proton magnetization is first turned 90 degrees by an rf pulse and, after time TE/2, 180 degrees by a second pulse. A spin echo will then be generated (S) at time TE. By adding additional 180 degree pulses a train of equally spaced echoes can be made (this is known as a Carr-Purcell sequence). The echoes will have a useful amplitude for a time of the order of the proton spin-spin relaxation time ($T_{2p}$) after the 90 degree pulse, this sets the practical number of echoes. Each echo is frequency coded by applying a coding gradient (X) in the (arbitrarily chosen) x-direction, during the sampling of the information contained in the echo. A second y-direction (normally perpendicular to x) is phase-coded by applying gradient pulse (Y) before each echo. Negative pulses of equal strength can be applied as shown after the echoes; this has been shown to make the result less sensitive to artefacts. The number of echoes (n) is chosen to be $n < T_{2p}/TE$. For $n=1$ one obtains the aforementioned saturation-recovery sequence and for $n>1$ one obtains a more rapid multiecho sequence. The sequence of FIG. 1 is repeated until the total number of echoes with different phase codings is equal to the desired number of lines in the y-direction of the image. The collected and stored data can be formed to a two dimensional image representing a projection of the object in the x-y-plane in a known fashion (e.g. by 2D-Fourier transform).

Usually an image representing either a slice or a 3-dimensional object is desired. To this end either a slice selecting gradient or a set of phase coding steps are added, correspondingly, in the z-direction. These methods are known to those familiar with the art.

The particular benefit of this procedure is that the polarization which was produced causes ΔA to be generated directly because the VHF excitation is interlaced with 180° RF pulses in such a way as to alternatingly add polarization corresponding to $H_{e1}$ and subtract polarization corresponding to $H_{e2}$.

Besides recording the ΔA data, data for an $\overline{A}$ image must generally be produced. In this case $H_{e1}$ and $H_{e2}$ alternate but without 180° RF pulses to give an average between them. The created polarization is subsequently coded and the FID signals are detected.

This is simply one among many ways of putting the method of the invention into operation.

However a novel and important part of this sequence is the method of integrating the desired ΔA information in the proton spin population by alternating different types of VHF radiation with 180° pulses. This method has the following advantages:

Firstly, it generates the difference signal ΔA almost continuously which makes it insensitive to disturbances and artefacts.

Secondly, it simultaneously gives an improved signal to noise (S/N) ratio for the ΔA image. This is because the difference signal can be recorded by one read-out of polarization rather than two read-outs as when making the difference at a later stage as in the previously described methods. This gives an improvement of the square root of 2 in S/N. Part of this advantage is lost if data for an $\overline{A}$ image has to be collected, but the loss is kept minimal by using only a small fraction of total time for collecting $\overline{A}$ data.

Thus viewed from a further aspect the invention provides a method of electron spin resonance enhanced magnetic resonance imaging of a paramagnetic substance-containing sample comprising sequentially exposing said sample to a first radiation of at least two frequencies selected to stimulate electron spin resonance transitions in said sample and to a second radiation of a frequency selected to stimulate coupled nuclear spin resonance transitions in said sample, preferably 180° pulses of said second (RF) radiation, whereby to cause said sample to emit a free induction delay signal from which a difference signal (ΔA) image of said sample may be generated. In this method, the imager is preferably also operated to generate data for a normalizing image ($\overline{A}$), for example by omitting the 180° RF pulses between the VHF pulses in otherwise identical pulse sequences (preferably interleaved with the ΔA data generating pulse sequences), and the imaging apparatus is preferably arranged to normalize the ΔA image, pixel by pixel, with the normalizing image so as to generate a normalized difference image.

Viewed from a yet further aspect the invention also provides an ESREMRI apparatus having means for exposing a sample to VHF radiation, means for exposing said sample to RF radiation and arranged to perform a method according to the invention, i.e. arranged to generate and detect FID signals under at least two sets of operational parameters and to generate therefrom an enhanced image of said sample. Such apparatus may be produced by straightforward modification of the apparatus of Leunbach or Lurie (supra).

I claim:

1. A method of electron spin resonance enhanced magnetic resonance imaging of a paramagnetic substance-containing sample, said method comprising: (i) detecting enhanced magnetic resonance signals from said sample under at least two different sets of operational parameters, said operational parameters including the timing of the exposure of said sample to magnetic field gradients and spin resonance stimulating radiations and the amplitude and frequency distribution of the electron spin resonance stimulating radiations; (ii) manipulating the detected signals to provide, for individual image elements, a normalized difference signal having a value proportional to the ratio between the difference between signal amplitude for said element under two different sets of said operational parameters and a mean signal amplitude for said element; and (iii) generating an image of at least part of said sample from said normalized difference signals.

2. A method of electron spin resonance enhanced magnetic resonance imaging of a paramagnetic substance-containing sample, said method comprising: (i) in repeated first pulse sequences, sequentially exposing said sample to a first radiation of at least two frequencies selected to stimulate electron spin resonance transitions in said sample and therebetween to 180° pulses of a second radiation of a frequency selected to stimulate coupled nuclear spin resonance transitions in said sample and subsequently further exposing said sample to at least one pulse of a second radiation whereby to cause the sample to emit magnetic resonance signals from which a difference signal ($\Delta A$) image of said sample may be generated; (ii) in repeated second pulse sequences interleaved with said first pulse sequences, exposing said sample to said first and second radiations as in said first pulse sequences but with the omission of said 180° second radiation pulses whereby to cause said sample to emit magnetic resonance signals from which a normalizing ($\overline{A}$) image of said sample may be generated; (iii) detecting magnetic resonance signals emitted from said sample in said first and second pulse sequences; and (iv) generating a normalized difference ($\Delta A/\overline{A}$) image from the detected magnetic resonance signals.

3. A method as claimed in claim 1 wherein the operational parameters which are varied to obtain said at least two sets of operational parameters include at least one of the amplitude and frequency of the electron spin resonance stimulating radiation.

4. A method as claimed in claim 1 wherein generation of the normalized difference signal is effected by proton polarization averaging.

5. A method as claimed in claim 1 wherein generation of the normalized difference signal is effected by echo subtraction.

* * * * *